United States Patent
Selman

[11] Patent Number: 5,842,466
[45] Date of Patent: Dec. 1, 1998

[54] STYLETTE END CAP

[76] Inventor: Corey M. Selman, 677 Barry Dr., Long Beach, Calif. 90805

[21] Appl. No.: 6,648

[22] Filed: Jan. 14, 1998

[51] Int. Cl.⁶ .................................................. A61M 16/00
[52] U.S. Cl. ............. 128/220.26; 128/912; 128/DIG. 26
[58] Field of Search ...................... 128/200.26, 207.29, 128/912, DIG. 26, 207.14, 207.17; 604/164, 256

[56] References Cited

U.S. PATENT DOCUMENTS

| | | | |
|---|---|---|---|
| D. 364,457 | 11/1995 | Mongeon | D24/127 |
| 2,438,679 | 3/1948 | Parker | 285/21 |
| 2,442,983 | 6/1948 | Nesset | 215/47 |
| 2,847,995 | 8/1958 | Adams | 128/214 |
| 3,688,773 | 9/1972 | Weiss | 128/207.29 |
| 3,741,217 | 6/1973 | Ciarico | 604/256 |
| 4,052,990 | 10/1977 | Dodgson | 128/351 |
| 4,112,932 | 9/1978 | Chiulli | 604/164 |
| 4,185,639 | 1/1980 | Linder | 128/200.26 |
| 4,246,897 | 1/1981 | Muto | 128/207.29 |
| 4,248,236 | 2/1981 | Linder | 128/349 B |
| 4,475,548 | 10/1984 | Muto | 128/207.14 |
| 4,595,005 | 6/1986 | Jinotti | 128/207.14 |
| 4,798,193 | 1/1989 | Giesy et al. | 604/164 |
| 4,909,798 | 3/1990 | Fleishhacker et al. | 604/256 |
| 4,938,746 | 7/1990 | Etheredge, III et al. | 128/200.26 |
| 4,981,464 | 1/1991 | Suzuki | 604/415 |
| 5,114,408 | 5/1992 | Fleischhaker et al. | 604/167 |
| 5,188,100 | 2/1993 | Miles et al. | 128/200.26 |
| 5,267,984 | 12/1993 | Doherty | 128/207.14 |
| 5,285,776 | 2/1994 | Bertram | 128/207.14 |
| 5,413,095 | 5/1995 | Weaver | 128/912 |
| 5,554,124 | 9/1996 | Alvarado | 604/167 |
| 5,569,205 | 10/1996 | Hart et al. | 604/167 |
| 5,634,908 | 6/1997 | Loomas | 604/167 |
| 5,642,726 | 7/1997 | Owens et al. | 128/207.14 |
| 5,657,963 | 8/1997 | Hinchliffe et al. | 251/149.1 |

Primary Examiner—Aaron J. Lewis

[57] ABSTRACT

A stylette or end cap connector for supporting a guide or stylette for medical tubing wherein the end cap is of integral tubular construction, and has a plurality of apertures through an enlarged head, and wherein an interior projection aids in friction fit retention with medical tubing, which is inserted therein.

7 Claims, 1 Drawing Sheet

STYLETTE END CAP

BACKGROUND OF THE INVENTION

1. Field of the Invention

The present invention relates generally to end caps utilized in conjunction with for example, endotracheal tubes or catheters and, in particular, to an end cap for use with stylettes or guides to act as a support and an abutment means to limit the travel of a catheter guide or endotracheal stylette.

2. Description of the Related Art

Stops have been disclosed in the prior art for endotracheal tubes and as catheter and stylette guides, which act to set the depth of penetration of the distal end of the guide or stylette into the endotracheal tube or catheter. These stops, in the past, have been of solid resilient material having a central bore extending completely through the solid stop which acts very much like a plug for the endotracheal tube.

In some instances, a hollow end, cap-like member has been proposed for supporting and, in a sense guiding, the catheter guide through and into the endotracheal or other tube with which the end cap may be utilized.

In practice, in the endotracheal tube setting, a guide taking the form of an elongated wand is inserted into and through a bore provided in the stop, and the stop is positioned at a preselected point in the length of the guide, with respect to its distal end, to predetermine the desired depth of penetration.

The proximal end portion of the guide is sometimes formed into a suitable handle and, therefore, must be malleable wherein the handle end is inserted into another aperture or recess in the stop to provide a means whereby the guide and associated, for example, endotracheal tube may be assembled for intubation of a patient requiring the medical procedure.

Prior art end caps have suffered in the context that they are either plug-like in configuration making them difficult to handle and associate with medical tubing or alternately, are either so thin-walled and flexible or stiff and hard as not to perform well with respect to allowing for specific-sized guides to be disposed therethrough and, ultimately, for proper disposition of the end-handled portion of for example, an endotracheal tube guide. In other instances, these end caps were not adequately dimensioned to be universally associable with medical-tubing of various diameters.

A search of related prior art yielded the following patents, some of which are relevant to the instant invention:

| PATENT | INVENTOR | ISSUED |
|---|---|---|
| D 342,134 | Mongeon, D. | Dec. 07, 1993 |
| D 364,457 | Mongeon, D. R. | Nov. 21, 1995 |
| 2,438,679 | Parker, A. L. | March 30, 1948 |
| 2,442,983 | Nesset, N. M. | June 08, 1948 |
| 2,847,995 | Adams, J. Q. | Aug. 19, 1958 |
| 4,052,990 | Dodgson | Oct. 11, 1977 |
| 4,185,639 | Linder | Jan. 29, 1980 |
| 4,248,236 | Linder | Feb. 03, 1981 |
| 4,475,548 | Muto | Oct. 09, 1984 |
| 4,909,798 | Fleischhacker et al | Mar. 20, 1990 |
| 4,981,464 | Suzuki | Jan. 01, 1991 |
| 5,114,408 | Fleischhaker et al. | May 19, 1992 |
| 5,285,776 | Bertram | Feb. 15, 1994 |
| 5,554,124 | Alvarado | Sep. 10, 1996 |
| 5,569,205 | Hart et al. | Oct. 29, 1996 |
| 5,634,908 | Loomas | Jun. 03, 1997 |
| 5,657,963 | Hinchliffe et al. | Aug. 19, 1997 |

Probably the most pertinent of the references are the Mongeon Design Patent No. 342,134, which shows and describes an end cap for medical tubing, which may be considered somewhat tubular in form. The actual device is of rigid, tubular plastic, which is not easily associable with medical tubing of various diameters and further, suffers in the context of having but a singular through-bore. Mongeon Design Patent No. 364,457 entitled Intubation End Cap, has but a singular through-bore and has, projecting components which makes it difficult to associate a guide therewith and further it being of rigid plastic makes it difficult to associate with the ends of medical tubing.

The other more pertinent end cap or stop, as it is termed in Linder U.S. Pat. No. 4,185,639, suffers in the context that it is of solid material, adding weight because of its solid nature and further, not being as universally associable with the medical tubing as the herein-disclosed invention and further, not having the versatility thereof.

SUMMARY OF THE INVENTION

The stylette connector cap of the present invention provides a hollow or tubular stylette support and connection for example, for an endotracheal tube, wherein the connector cap comprises the combination of a tubular, elastomeric member of flexible, thin-wall construction having a first open end adapted to receive an elongate endotracheal tube in friction fit engagement therewith and having a second end of substantially closed wall construction with a plurality of spaced through bores of different diameters to receive one of a selected size stylette therethrough in supportive relationship therewith. The second end of the cap member has an interior, depending integral projection about a minor portion of the circumference of the interior of said second end, and is spaced away from the plurality of spaced through bores, which provides easy friction fit association with for example, the end of a medical tube. The terminus of the wall of the said first open end is radiused for ease of connection, and as indicated the tubular elastomeric member is flexible and pliable having a durometer rating of between 20–90 on the A scale with the preferred being 50–70 on the A scale.

With the above-disclosed stylette connector cap, it is possible to have universal capability of association with medical tubing wherein a wide range of medical tubing, relatively speaking, may be associated with the end cap because of an interior depending projection on leg member, which provides for friction fit retention interiorly of the end cap, and for disposition of the end cap over the external portion of the medical tube with which the end cap is associated.

Additionally, the end cap has a plurality of spaced apertures which allows for guides or stylettes of various sized diameters to be placed therethrough, and also provides a convenient method of retaining the end of a malleable guide which may be handle-shaped or configured so that the free end is received in one of the through holes or bores of the end cap.

OBJECTS OF THE INVENTION

It is another object of the present invention to provide an end cap for medical tubes and the like.

It is another object of the invention to provide an end cap for medical tubes which provides a plurality of apertures through which a guide member may be inserted.

It is still another important, additional object of the invention to provide a connector cap for endotracheal tubes for example, which supports a stylette or guide therein.

It is yet another important object of the invention to provide a connector cap of tubular elastomeric material of flexible thin-walled construction, having almost universal adaptability with various diameter medical tubes.

It is yet another important object of the invention to provide an easily manufactured, low cost medical tube end cap which may be utilized to support a guide or stylette and also provide a means of anchoring the proximate end of the guide or stylette. These and other objects and advantages of the present invention will become apparent from the following specification and accompanying drawings.

DESCRIPTION OF THE PREFERRED EMBODIMENT(S)

Figure 2:
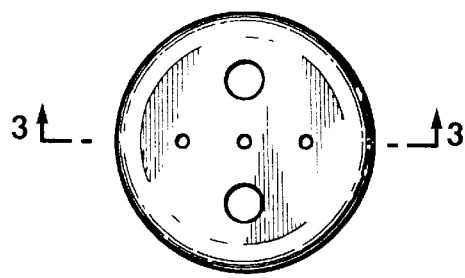
FIG. 2 is a top view thereof.
Figure 1:
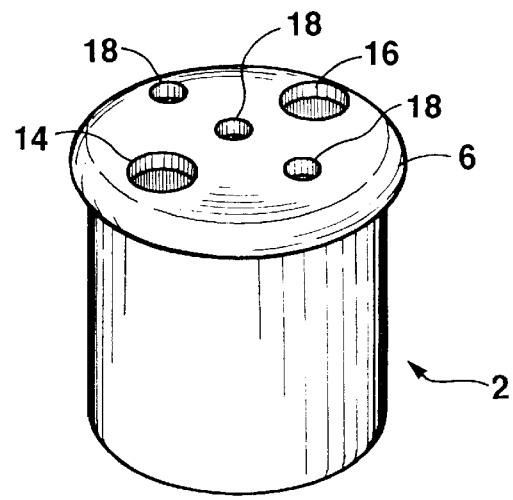
FIG. 1 is a perspective view of the stylette connector cap.
Figure 3:
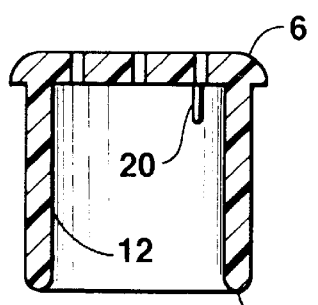
FIG. 3 is a cross-sectional view taken along the line of 3—3 of FIG. 2.
Figure 4:
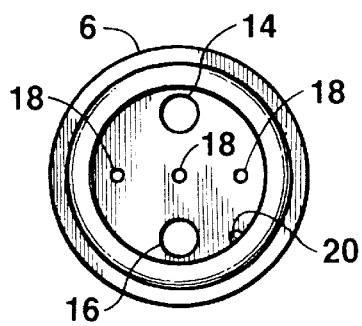
FIG. 4 is a bottom view of the stylette connector cap shown in FIG. 1.
Figure 5:
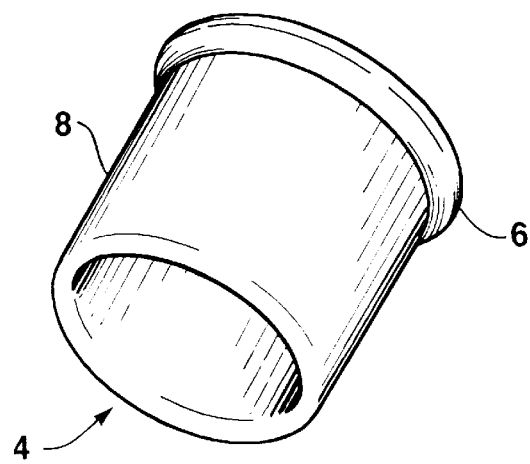
FIG. 5 is a bottom perspective view thereof.

Referring to the drawings wherein like numerals of reference refer to like elements throughout, it will be noted that the connector cap or stylette connector cap 2 is of integral construction of elastomeric or the like materials, which is somewhat flexible or pliable, preferably having a durometer rating of between 20–90 on the A scale. The end cap 2 has a first open end 4 of sufficient diameter to receive the end for example, of an endotracheal tube. Opposite open end 4 is outwardly flaring end 6 having what may be considered an outwardly flared head 6 by which the end cap may be easily manipulated with fingers of the hand of the user.

It will be noted that end cap 2 is of tubular construction with flexible sidewalls 8 terminating in rounded radius edge 10. The interior wall 12 has a slight draft of about 1° which is required in the molding process, and which further allows for easily associating the end cap 2 with the termini of medical tubing or the like.

The second or closed end 6 is provided with two spaced through bores 14 and 16 of the same diameter and having about the diameter of stylettes or guides found in the endotracheal art for reasons that will be further described.

Along the diameter line of the head 6 are three smaller spaced apertures 18 to receive small diameter guides or stylettes, that those in the medical profession will recognize.

Interiorly, of the cap 2 and positioned about 45° from aperture 18 and aperture 16, is depending integral leg or projection 20 along a minor portion of the circumference of the interior of end cap 2.

In the end cap 2 shown as an example, the same is a 15 millimeter female stylette connector made of for example, PVC, of medical grade, and wherein apertures 14 and 16, for example, may be about 6 millimeters in diameter, with apertures 18 being about 3 millimeters in diameter.

It is, of course, well-recognized that these through bores and apertures may be of various sizes in keeping with the desired end results to be achieved with the stylette connector cap of the invention.

Figure 6:
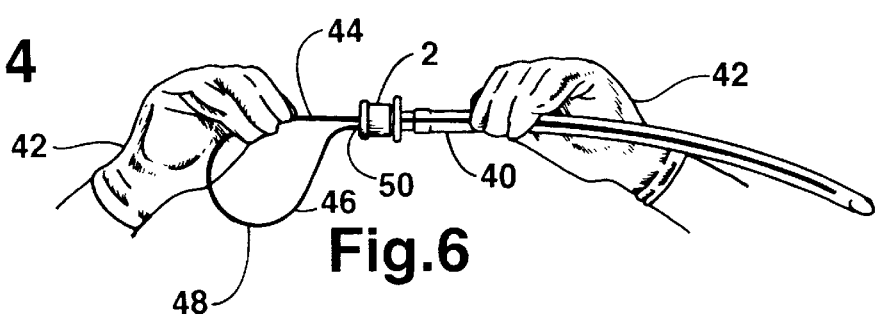
FIG. 6 is a schematic illustration showing how the end cap of the invention is used with an endotracheal tube and stylette.

Referring to FIG. 6, it will be seen that the end cap 2 is associated with medical tube 40, which in this instance is an endotracheal tube. FIG. 6, also shows the mode of manipulation by the hands 42 of a medical technical or the like. In this instance, the stylette or guide 44 is positioned through through bore 16 and inserted a predetermined length within the tube 40. The proximal end 46 of the stylette or guide 44 is bent in the shape of a handle portion 48 with the terminus 50 being fashioned and maneuvered to fit into opposed through bore 14 so that a complete assemblage is now ready for intubation of a patient.

Thus, in using the end cap, one would insert the stylette 44 into the endotracheal tube 40 to within about one-quarter inch of the distal tip. The end of the medical tube is then pushed into the interior of tubular end cap 2 and held in friction fit, releasable engagement by reason of sidewalls 12 and depending leg or projection 20. The end 46 of stylette 44, is then bent into an acute right angle to form the handle as 48. Thereafter the free end 50 is secured into the through bore 14.

The end cap 2 as shown herein may have an interior diameter of about 0.610 inch with the outside diameter of head 6 being about 0.810 inch and an overall length of about 0.75 inch. The interior leg or projection extends about 0.125 inch as measured from the underside or interior of cap 2. The interior length of cap 2 is about 0.687 inch. Thus, a preferable ratio of leg or projection 20 length to the interior of cap 2 is about 1:4 to 1:6 with the preferred being about 1:5.5.

In the preferred embodiments of the invention, the upper surface of head 6 is shown as flat, but may be domed or concave as well, and while a plurality of apertures or through bores has been shown, those of ordinary skill in the art that these may be decreased or increased as the need arises. Additionally, while PVC material has been described as a material of construction, and has been described as being integrally-formed, those of ordinary skill in the art will recognize that the end cap of the invention may be made differently and indeed, materials of construction may be different; although as indicated, it is preferred to have a flexible thin-walled material preferably with a durometer rating of 50–70 on the A scale.

While the present invention has been described with regard to particular embodiments, it should be recognized by those of ordinary skill in the art that various modifications and adaptations will make themselves apparent, all of which will not depart from the invention as defined in the appended claims.

I claim:

1. A connector cap for providing stylette support and connection to an endotracheal tube comprising the combination of:

a tubular, elastomeric member of flexible thin wall construction having a first open end adapted to interiorally receive an elongate endotracheal tube in friction fit engagement therewith and a second end of substantially closed wall construction and having a plurality of spaced, through bores to receive one of a selected size stylette therethrough in supportive relationship therewith, said second end having an interior, depending integral projection about a minor portion of a circumference of the interior of said second end, and being spaced away from said plurality of spaced, through bores, said first open end being radiused and said tubular elastomeric member being pliable and having a durometer rating of between 20–90 on the A scale.

2. The connector cap in accordance with claim 1 wherein the connector cap is integrally formed of a material which has a durometer rating of between 50–70 on the A scale.

3. The connector cap in accordance with claim 2 wherein there are at least two opposed through bores, one of which is adapted to receive a stylette therethrough and the opposed through bore is adapted to receive a proximate end of such a stylette which may be shaped into a handle.

4. The connector cap in accordance with claim 3 wherein said interior depending integral projection is spaced at least 45° from any one of the plurality of space through bores.

5. The connector cap in accordance with claim 4 wherein at least two of the through bores are of the same diameter.

6. The connector cap in accordance with claim 5 wherein smaller-spaced through bores are provided running along the diameter of said tubular connector cap.

7. A connector cap for providing stylette support and connection to an endotracheal tube comprising the combination of:

a tubular, elastomeric member of flexible thin wall construction having a first open end adapted to interiorally receive an elongate endotracheal tube in friction fit engagement therewith and an outwardly flared second end of substantially closed wall construction and having at least two like-sized, spaced through bores to receive a stylette therethrough in supportive relationship therewith, said outwardly flared second end having an interior, depending integral projection about a minor portion of a circumference of the interior of said second end, and extending inward along the length of the interior surface of said end cap and being spaced away from said at least two-like-sized, spaced through bores, said first open end being radiused and said tubular elastomeric member being pliable and having a durometer rating of between 20–90 on the A scale.

\* \* \* \* \*

UNITED STATES PATENT AND TRADEMARK OFFICE
CERTIFICATE OF CORRECTION

PATENT NO. : 5,842,466

DATED : December 1, 1998

INVENTOR(S) : Selman, Corey M.

It is certified that error appears in the above-identified patent and that said Letters Patent is hereby corrected as shown below:

On title page insert -- item [73] Assignee: Polamedco, Inc.
4054 Glencoe Avenue
Marina del Rey, California 90292

Signed and Sealed this

Twenty-eighth Day of November, 2000

Attest:

Q. TODD DICKINSON

Attesting Officer

Director of Patents and Trademarks